US00PP16028P2

(12) United States Plant Patent
Hambali

(10) Patent No.: US PP16,028 P2
(45) Date of Patent: Oct. 11, 2005

(54) ***CALATHEA* PLANT NAMED 'INDRI'**

(50) Latin Name: ***Calathea loesenerii*×*C. roseo picta***
Varietal Denomination: Indri

(75) Inventor: Gregori G. Hambali, Baranangsiang Indah Bogor (ID)

(73) Assignee: Twyford International, Inc., Santa Paula, CA (US)

( * ) Notice: Subject to any disclaimer, the term of this patent is extended or adjusted under 35 U.S.C. 154(b) by 70 days.

(21) Appl. No.: 10/955,477

(22) Filed: Sep. 30, 2004

(51) Int. Cl.[7] ..... A01H 5/00
(52) U.S. Cl. ..... Plt./375
(58) Field of Search ..... Plt./375

(56) References Cited

U.S. PATENT DOCUMENTS

| | | | | | |
|---|---|---|---|---|---|
| PP9,621 | P | * | 8/1996 | Lamb | Plt./375 |
| PP10,898 | P | * | 5/1999 | van Rijn | Plt./375 |
| PP12,736 | P2 | * | 7/2002 | Lamb | Plt./375 |

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Calathea* plant named 'Indri', characterized by its upright and broad outwardly spreading growth habit; elliptic-shaped dark green and metallic silver green-colored leaves often variably tinged with pink when developing; and long-lasting inflorescences with green and pink-colored bracts held above the foliage on strong scapes.

3 Drawing Sheets

Botanical designation: *Calathea loesenerii*×*C. roseo picta.*
Variety denomination: 'Indri'.

CROSS-REFERENCE TO RELATED APPLICATIONS

The present application is co-pending with U.S. Plant patent application Ser. No. 10/955,483, filed Oct. 1, 2004, titled: "*Calathea* Plant Named 'Mia'".

BACKGROUND OF THE INVENTION

The present Invention relates to a new and distinct cultivar of *Calathea* plant, botanically known as *Calathea loesenerii*×*C. roseo picta,* and hereinafter referred to by the name 'Indri'.

The new *Calathea* is a product of a planned breeding program conducted by the Inventor in Bogor, Indonesia. The objective of the breeding program is to create new flowering *Calathea* cultivars with a plant habit appropriate for container production, desirable flowering habit and color and good postproduction longevity.

The new *Calathea* originated from a cross-pollination made by the Inventor in Bogor, Indonesia in July, 1996, of an unnamed selection of *Calathea loesenerii,* not patented, as the female, or seed, parent with the *Calathea roseo picta* cultivar Eclipse, (U.S. Plant Pat. No. 9,621), as the male, or pollen, parent. The cultivar Indri was discovered and selected by the Inventor as a single plant within the progeny of the stated cross-pollination in a controlled environment in Bogor, Indonesia in December, 1998.

Asexual reproduction of the new *Calathea* by divisions in a controlled environment in Bogor, Indonesia since April, 1999, has shown that the unique features of this new *Calathea* are stable and are reproduced true to type in successive generations. Asexual reproduction of the new *Calathea* by tissue culture done in a laboratory in Sebring, Fla. since Spring, 2000, has also confirmed that the unique features of this new *Calathea* are stable and are reproduced true to type in successive generations.

SUMMARY OF THE INVENTION

Plants of the cultivar Indri have not been observed under all possible environmental conditions. The phenotype may vary somewhat with variations in environment such as temperature and/or light intensity without, however, any variance in genotype.

The following traits have been repeatedly observed and are determined to be the unique characteristics of 'Indri'. These characteristics in combination distinguish 'Indri' as a new and distinct cultivar:

1. Upright and broad outwardly spreading growth habit.
2. Elliptic-shaped dark green and metallic silver green-colored leaves often variably tinged with pink when developing.
3. Long-lasting inflorescences with green and pink-colored bracts held above the foliage on strong scapes.

Plants of the new *Calathea* can be compared to the female parent, the unnamed selection of *Calathea loesenerii.* However plants of the new *Calathea* differ from plants of the female parent selection in the following characteristics:

1. Plants of the new *Calathea* are shorter and more outwardly spreading than plants of the female parent selection.
2. Plants of the new *Calathea* have larger leaves than plants of the female parent selection.
3. Plants of the new *Calathea* and the female parent selection differ in leaf coloration.

Plants of the new *Calathea* are most similar to plants of the male parent, the cultivar Eclipse. However plants of the new *Calathea* differ from plants of the cultivar Eclipse in the following characteristics:

1. Plants of the new *Calathea* are taller and more upright than plants of the cultivar Eclipse.

2. Plants of the new *Calathea* have larger leaves than plants of the cultivar Eclipse.
3. Flowers of plants of the new *Calathea* have green and pink-colored bracts whereas flowers of plants of the cultivar Eclipse have green-colored bracts.
4. Flowers of plants of the new *Calathea* have longer scapes than flowers of plants of the cultivar Eclipse.

Plants of the new *Calathea* can also be compared to plants of the *Calathea* hybrid cultivar Mia (U.S. Plant patent application Ser. No. 10/955,483, filed Oct. 1, 2004). Plants of the new *Calathea* and the cultivar Mia differ primarily in leaf and flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Calathea.*

The photograph on the first sheet comprises a side perspective view of a typical plant of 'Indri' grown in a container.

The photograph on the second sheet comprises a side perspective view of a typical flowering plant of 'Indri' grown in a container.

The photograph on the third sheet is a close-up view of a typical inflorescence of 'Indri'.

DETAILED BOTANICAL DESCRIPTION

Plants used for the aforementioned photographs and the following description were about 12 months old and grown in 15-cm containers in Apopka, Fla., in a polyethylene-covered greenhouse with day temperatures ranging from 24 to 35° C., night temperatures ranging from 18 to 24° C. and light levels about 1,500 foot-candles.

All color references are measured against The Royal Horticultural Society Colour Chart, 1995 Edition. Colors and numerical measurements are approximate as plant growth and development depends on environmental conditions and cultural practices such as light level and temperature, among others, without, however any variance in genotype.

Botanical classification: *Calathea loesenerii⨯C. roseo picta* cultivar Indri.

Parentage:

*Female, or seed, parent.*—Unnamed selection of *Calathea loesenerii,* not patented.

*Male, or pollen, parent.*—*Calathea roseo picta* cultivar Eclipse, disclosed in U.S. Plant Pat. No. 9,621.

Propagation:

*Type.*—By tissue culture.

*Time to initiate roots on tissue-cultured plants.*—Summer: About two weeks at temperatures of 26° C. Winter: About three weeks at temperatures of 21° C.

*Time to produce a rooted tissue-cultured plant.*—Summer: About ten weeks at 26° C. Winter: About 13 weeks at 21° C.

*Root description.*—Main roots, fibrous; lateral roots, fine; dark brown in color.

Plant description:

*Form.*—Upright and broad outwardly spreading growth habit; freely clumping, leaves emerging from the base in a rosette; about five to eight axillary branches per plant.

*Plant height, soil level to top of plant plane.*—About 28 to 33 cm.

*Plant width.*—About 40 to 47 cm.

*Petiole description.*—Aspect: Upright. Length: About 12 to 18 cm. Diameter: About 5 mm. Texture, upper and lower surfaces: Smooth. Color: 187A. Leaf sheath: Length: About 2 to 8 cm. Width: About 8 mm. Apex: Tapering and becoming flush with the petiole. Texture, upper and lower surfaces: Fleshy. Color: 187A. Geniculum: Length: About 2.8 cm. Width: About 5 mm. Aspect: During the night and early morning, the geniculum is straight or slightly curved; during the day, the geniculum is bent about 90°. Texture, upper and lower surfaces: Smooth. Color: 187A tinged with 199A.

*Foliage description.*—Arrangement: Alternate, simple. Length: About 20 cm. Width: About 13 cm. Shape: Elliptic. Apex: Acuminate. Base: Obtuse. Margin: Entire; undulate. Texture, upper and lower surfaces: Smooth, glabrous; slightly leathery. Midrib is thick and prominent; midrib recessed on the upper leaf surface and protruding from the lower surface. Primary veins are recessed in the leaf blade; leaf blade is concave between the primary veins. Venation pattern: Pinnate. Color: Developing foliage, upper surface: Center, 137B; border towards the margin, a mix of 194C and 191B; midrib, 147C mixed with 146C; primary veins, 147C; leaf often variably tinged with 58A. Developing foliage, lower surface: 187A; midrib, 177A tinged with 187A; primary veins, 187A. Fully expanded foliage, upper surface: Center, 137A; border towards the margin, a mix of 194B and 191A; midrib, 147C mixed with 146C; primary veins, 147C. Fully expanded foliage, lower surface: 187A; midrib, 177A tinged with 187A; primary veins, 187A.

Inflorescence description:

*Natural flowering season.*—Plants of the new *Calathea* begin flowering in April in Apopka, Fla.

*Inflorescence/flower longevity.*—Inflorescences maintain good color for about ten weeks on the plant. Individual flowers last about one day on the plant.

*Type/arrangement.*—Tall, terminally bracted spike. About 30 to 36 cm in height. Flower bracts are arranged in closely-spaced vertical ranks and occupy the uppermost 6 cm of the spike. About seven terminal bracts and about ten lower bracts with underlying flowers.

*Terminal bract shape.*—Ovate; apex, acute; margin, entire.

*Lower bract shape.*—Obovate; apex, emarginate; margin, entire.

*Terminal bract length.*—About 4.2 to 5.2 cm.

*Lower bract length.*—About 2.5 cm.

*Terminal bract width.*—About 1.9 to 2.7 cm.

*Lower bract width.*—About 2.5 cm.

*Terminal and lower bract texture, upper and lower surfaces.*—Smooth.

*Terminal bract color, immature, upper and lower surfaces.*—146D; towards the margins, 65B to 65C.

*Terminal bract color, mature, upper and lower surfaces.*—146C to 146D; towards the margins, tinged with 59D; towards the base, 155D flushed with 146D.

*Lower bract color, immature, upper and lower surfaces.*—146D; towards the margins, 65B to 65C.

*Lower bract color, mature, upper and lower surfaces.*—155D flushed with 146D; towards the margins, 59D.

*Flowers.*—Arrangement: Borne in short branch spikes under the lower bracts. Each branch spike contains about four flowers or buds. About 45 flowers/buds per inflorescence. Calyx and corolla mostly concealed under bracts; staminodes, style and anther prominently displayed. Calyx: Quantity of sepals per flower: Three. Length: About 1.5 cm. Width: About 2.5 mm. Color: 155D. Corolla: Quantity of petals per flower: Three. Length: About 3 cm. Width: About 4 mm. Color: 155D.

*Staminodes.*—Quantity per flower: Three. Length: Two staminodes, about 3.5 cm; third staminode, about 3.1 cm. Width: About 4 mm. Color: Two staminodes, about 155D; third staminode, 155D, towards the apex, 79D.

*Reproductive organs.*—Stamen quantity per flower: One. Filament length: About 2.2 cm. Anther length: About 2.5 mm. Anther color: 9D. Style length: About 3 cm. Style color: 155D. Ovary: Inferior, three-celled. Ovary length: About 3 mm. Ovary color: 158B.

*Scapes.*—Length: About 28 cm. Diameter: About 3 mm. Aspect: Erect. Strength: Strong. Texture: Smooth. Color: 187A tinged with 177A.

Disease/pest resistance: Under commercial production conditions, plants of the new *Calathea* have not been noted to be resistant to pathogens or pests common to *Calathea*.

Temperature tolerance: Plants of the new *Calathea* have been observed to tolerate temperatures from 6 to 40° C. in Apopka, Fla.

It is claimed:

1. A new and distinct cultivar of *Calathea* plant named 'Indri', as illustrated and described.

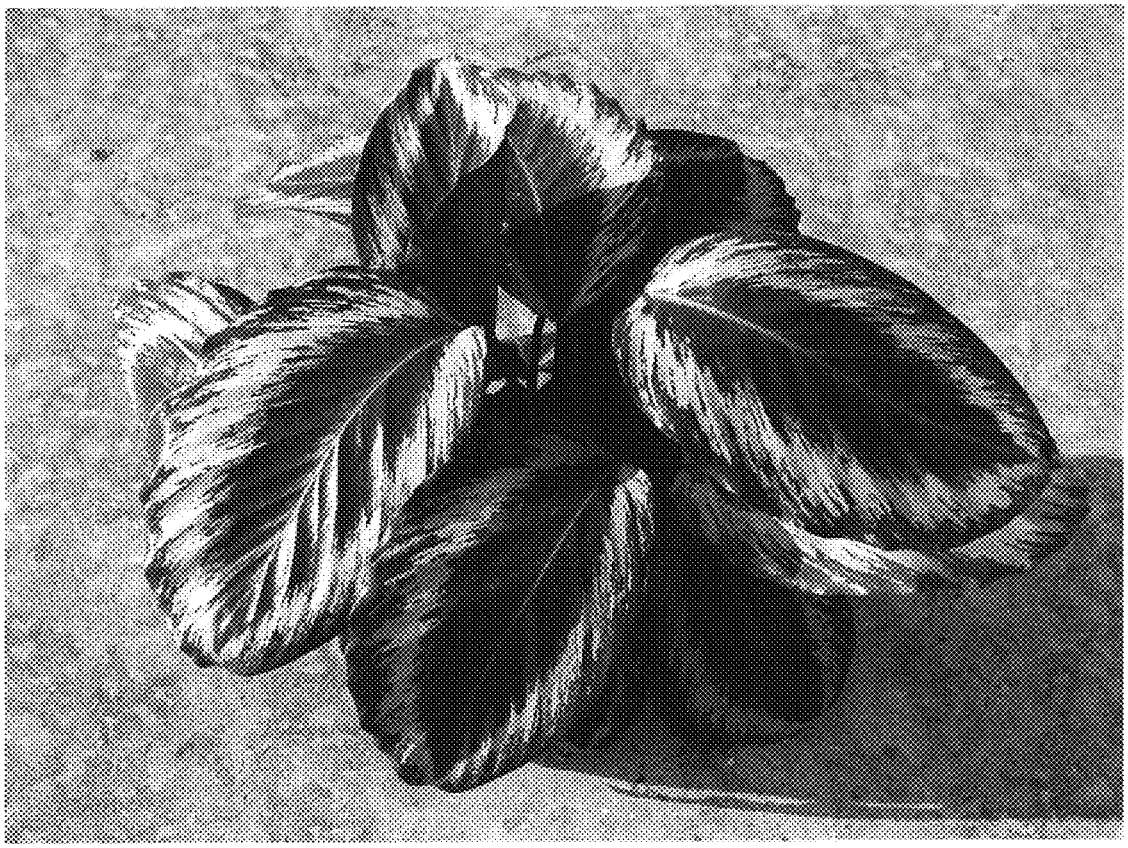

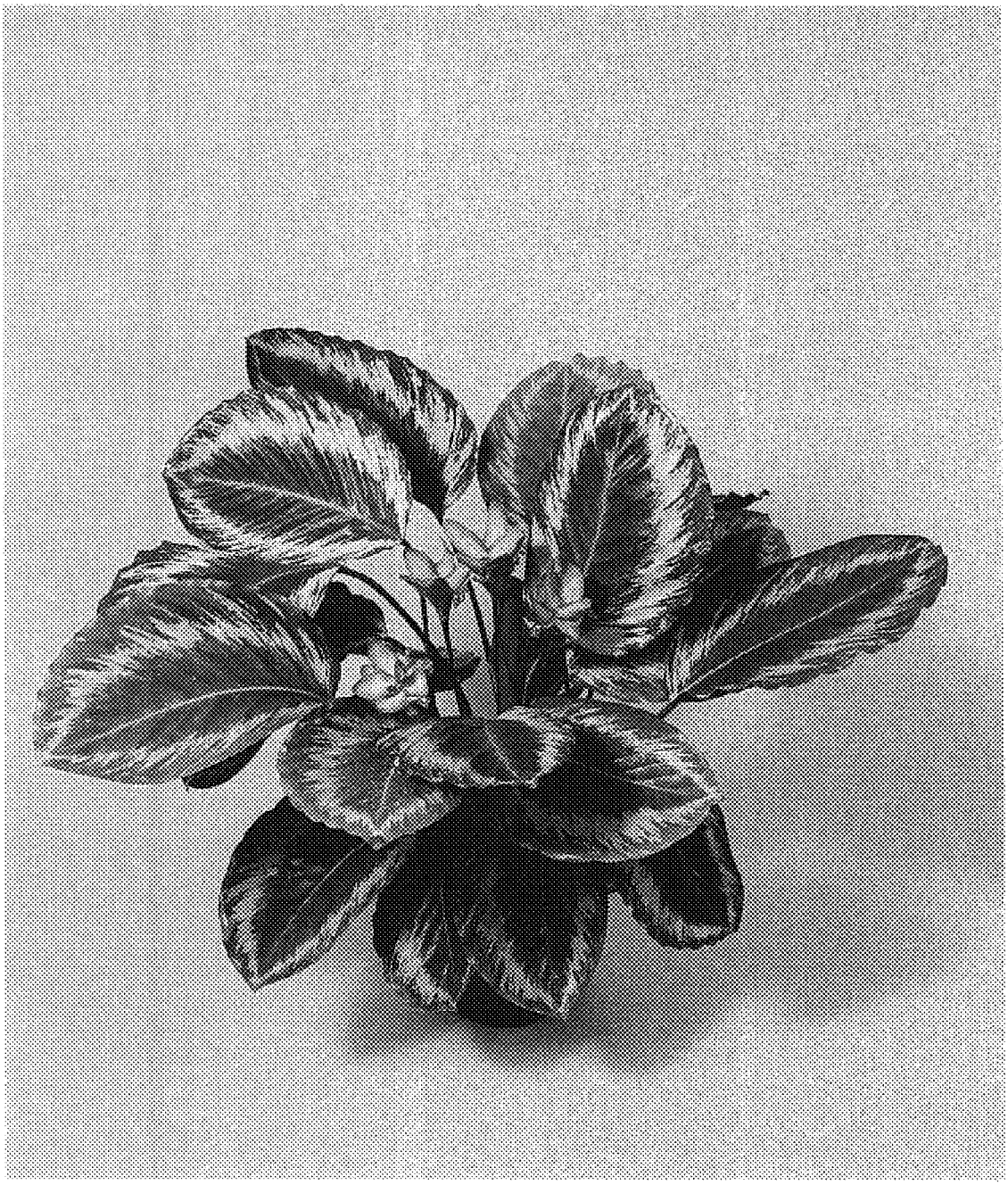

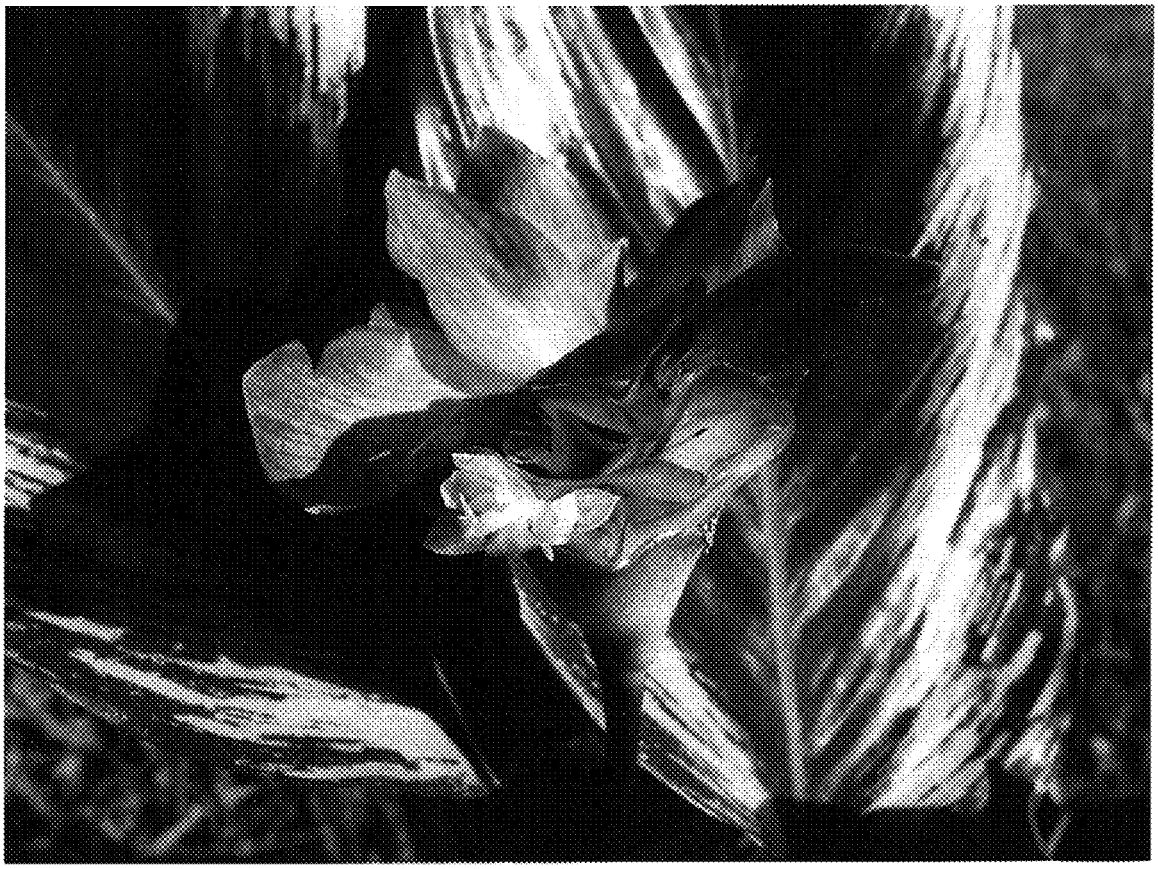

* * * * *